United States Patent
Maurin et al.

(10) Patent No.: US 6,306,886 B1
(45) Date of Patent: *Oct. 23, 2001

(54) CRYSTALLINE ROXIFIBAN

(75) Inventors: Michael Blaise Maurin, Wilmington, DE (US); Philip Ma, Chadds Ford, PA (US); David John Meloni, Newark, DE (US); Jaan A. Pesti, Wilmington, DE (US); Lucius Thomas Rossano, Newark, DE (US); Randall K. Ward, Wilmington, DE (US); Jianguo Yin, Hockessin, DE (US); Lin Hua Zhang, New Fairfield, CT (US); Goss S. Kauffman, Bear, DE (US)

(73) Assignee: DuPont Pharmaceuticals Company, Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/094,944

(22) Filed: Jun. 15, 1998

Related U.S. Application Data

(60) Provisional application No. 60/080,278, filed on Apr. 1, 1998, provisional application No. 60/049,712, filed on Jun. 16, 1997, and provisional application No. 60/049,633, filed on Jun. 16, 1997.

(51) Int. Cl.$^7$ .................. A61K 31/12; C07D 261/04; A61P 7/02
(52) U.S. Cl. ............................. 514/378; 548/240
(58) Field of Search ............................ 548/240; 514/378

(56) References Cited

U.S. PATENT DOCUMENTS 5,849,736 * 12/1998 Wityak ........................ 514/227.8

FOREIGN PATENT DOCUMENTS

WO9514683  6/1995  (WO).

OTHER PUBLICATIONS

Zhang et al., Tetrahedon Letters, 1996, 37 (26), 4455–58.
Zhang et al., J. Org. Chem, 1997, 62 (8), 2466–2470.

* cited by examiner

*Primary Examiner*—Evelyn Mei Huang

(57) ABSTRACT

The potent platelet glycoprotein IIb/IIIa antagonist, roxifiban, is produced in crystalline form. Crystalline roxifiban exists in two polymorphic forms, designated Form 1 and Form 2. These polymorphic forms are characterized by x-ray powder diffraction and solid-state carbon NMR. Pharmaceutical compositions and methods for the treatment or prevention of diseases mediated by platelet aggregation are described.

30 Claims, 4 Drawing Sheets

CRYSTALLINE ROXIFIBAN

This application claims the benefit of U.S. Provisional Application Ser. No. 60/049,712, filed Jun. 16, 1997; U.S. Provisional Application Ser. No. 60/049,633, filed Jun. 16, 1997; and U.S. Provisional Application Ser. No. 60/080,278, filed Apr. 1, 1998.

FIELD OF THE INVENTION

The potent platelet glycoprotein IIb/IIIa antagonist, roxifiban, is produced in crystalline form. Crystalline roxifiban exists in two polymorphic forms, designated Form 1 and Form 2. These polymorphic forms are characterized by x-ray powder diffraction and solid-state carbon NMR. Pharmaceutical compositions and methods for the treatment or prevention of diseases mediated by platelet aggregation are described.

BACKGROUND OF THE INVENTION

The present invention relates to crystalline forms of a potent platelet glycoprotein IIb/IIIa antagonist known as roxifiban. Roxifiban is an acetate salt methyl ester prodrug form of a potent platelet glycoprotein IIb/IIIa antagonist. It is a non-peptide isoxazoline compound represented by the following structural formula:

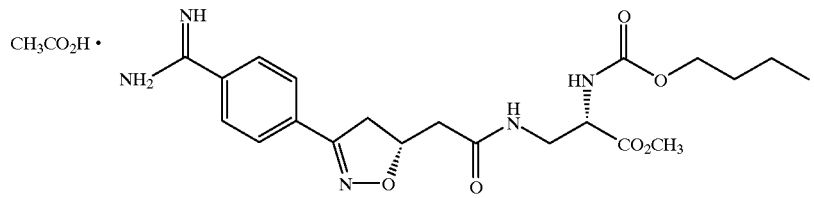

Roxifiban is known by its chemical name, methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt. Roxifiban is encompassed within the description and claims of Patent Cooperation Treaty application number PCT/US94/13155 (International Publication Number WO 95/14683) filed on Nov. 14, 1994, the disclosure of which is incorporated herein by reference. This international patent application claims priority from U.S. Ser. No. 08/157,598, filed Nov. 24 1993, U.S. Ser. No. 08/232,961, filed Apr. 22, 1994 and U.S. Ser. No. 08/337,920, filed Nov. 10, 1994, the disclosure of each of which is incorporated herein by reference. The synthesis of the trifluoroacetic acid salt of the prodrug base of roxifiban is described in Example 314B of PCT/US94/13155.

The active component of roxifiban has been found to inhibit the binding of soluble adhesive proteins, such as fibrinogen, von Willebrand factor, fibronectin and vitronectin, to the platelet glycoprotein IIb/IIIa complex. As a consequence, the compound is capable of inhibiting the activation and aggregation of platelets induced by all known endogenous platelet agonists. roxifiban is, therefore, useful for the treatment or prevention of thromboembolic disorders including thrombosis or embolus formation, harmful platelet aggregation, reocclusion following thrombolysis, reperfusion injury, restenosis, atherosclerosis, stroke, myocardial infarction and unstable angina. Other diseases that involve cell adhesion processes may also be treated by the administration of roxifiban. Such diseases include, for example, rheumatoid arthritis, asthma, allergies, adult respiratory syndrome, organ transplantation rejection, septic shock, psoriasis, contact dermatitis, osteoporosis, osteoarthritis, tumor metastatis, diabetic retinopathy, inflammatory conditions and inflammatory bowel disease.

Treatment or prevention of the foregoing disorders is accomplished by administering a therapeutically effective amount of roxifiban to a human or animal subject in need of such treatment or prevention. The compound may be administered enterally or parenterally in solid or liquid dosage forms. In general dosages of from about 0.001 to about 10 mg/kg of body weight per day, preferably from about 0.005 to about 1 mg/kg of body weight per day are employed.

The synthesis of roxifiban and its recovery as a substantially pure crystalline product are described by Zhang et al., *Tetrahedron Letters*, 37(26), 4455–58 (1996); Zhang et al., *J. Org. Chem.*, 62(8), 2469 (1997). Roxifiban has not been known previously to exist in stable crystalline polymorphic forms.

For the manufacture, purification and formulation of roxifiban, the drug advantageously is produced in a crystalline form. Accordingly, a need exists for stable crystalline forms of the drug and reliable and reproducible procedures for their manufacture.

SUMMARY OF THE INVENTION

In one aspect, the present invention is directed to crystalline roxifiban. A related aspect resides in novel crystalline polymorphs of roxifiban, designated Form 1 and Form 2. The Form 1 polymorph has been characterized and distinguished from the Form 2 polymorph by solid-state carbon NMR and powder X-ray diffraction analysis.

Further aspects of the invention involve pharmaceutical compositions of crystalline roxifiban and its Form 1 and Form 2 polymorphs. The crystalline prodrug products of this invention may be formulated into conventional solid pharmaceutical dosage forms or used for the preparation of liquid dosage forms by combining a therapeutically effective amount of the crystalline prodrug with a pharmaceutically acceptable carrier. In another aspect, the present invention involves a method for inhibiting the binding of a soluble adhesion protein to the platelet glycoprotein IIb/IIIa complex which comprises administering an amount of crystalline roxifiban sufficient to result in the platelet glycoprotein IIb/IIIa being contacted with an effective inhibitory amount of the active drug substance. In particular aspects, the invention involves methods for treating or preventing various thromboembolic disorders and other disorders involving cell adhesion, which comprise administering a therapeutically effective amount of a pharmaceutical composition comprising the novel crystalline forms of roxifiban of this invention.

BRIEF DESCRIPTION OF THE DRAWINGS

The invention is illustrated by reference to the accompanying drawings desribed below.

DETAILED DESCRIPTION OF THE INVENTION

In a first embodiment, the present invention provides crystalline roxifiban in substantially pure form.

In a more preferred embodiment, the crystalline roxifiban is greater than 90 percent pure.

In a second embodiment, the present invention provides the Form 1 polymorph of crystalline roxifiban in substantially pure form.

In a more preferred embodiment, the Form 1 crystalline roxifiban is greater than 90 percent pure.

In another preferred embodiment, the Form 1 polymorph is characterized by a solid-state $^{13}$C CP/MAS NMR spectrum having a doublet of peaks at 63 and 66 ppm.

In a more preferred embodiment, the solid-state $^{13}$C CP/MAS NMR spectrum of the Form 1 polymorph has a doublet of peaks at 19 and 21 ppm.

Figure 1:
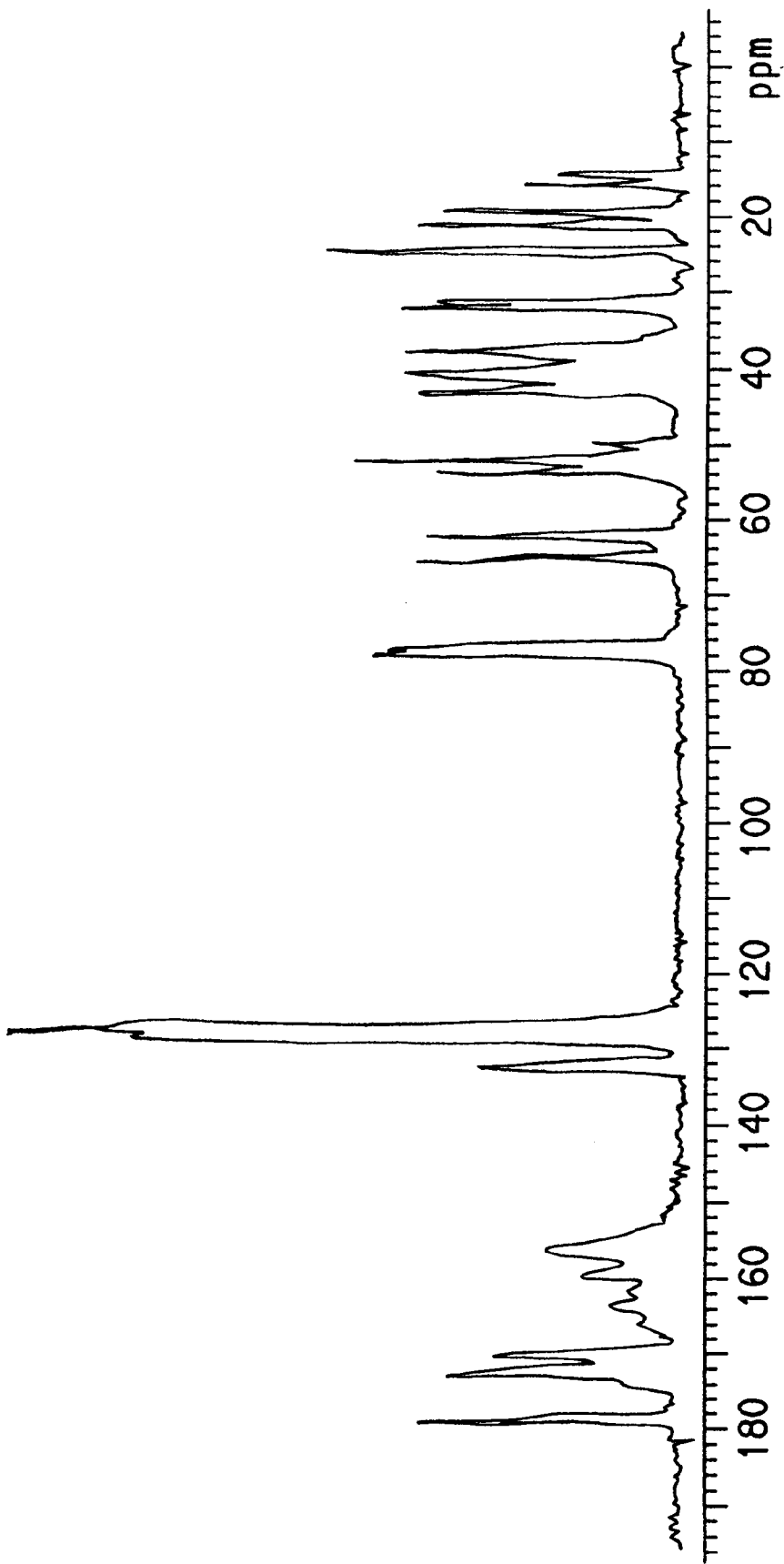
FIG. 1 is a solid-state $^{13}$C CP/MAS NMR spectrum of the Form 1 crystalline polymorph of roxifiban.

In another preferred embodiment, the Form 1 polymorph of crystalline roxifiban, has a solid-state $^{13}$C CP/MAS NMR spectrum substantially in accordance with that shown in FIG. 1.

In another preferred embodiment, the Form 1 polymorph is characterized by an x-ray powder diffraction pattern comprising 2θ values of 6.4±0.2, 9.6±0.2, 12.5±0.2, 14.7±0.2, 19.3±0.2, 21.5±0.2, 22.5±0.2, 23.2±0.2, 25.2±0.2, 27.5±0.2, and 32.2±0.2.

In a more preferred embodiment, the x-ray powder diffraction pattern of the Form 1 polymorph is substantially devoid of a peak at 2θ of 13.6±0.2.

Figure 3:
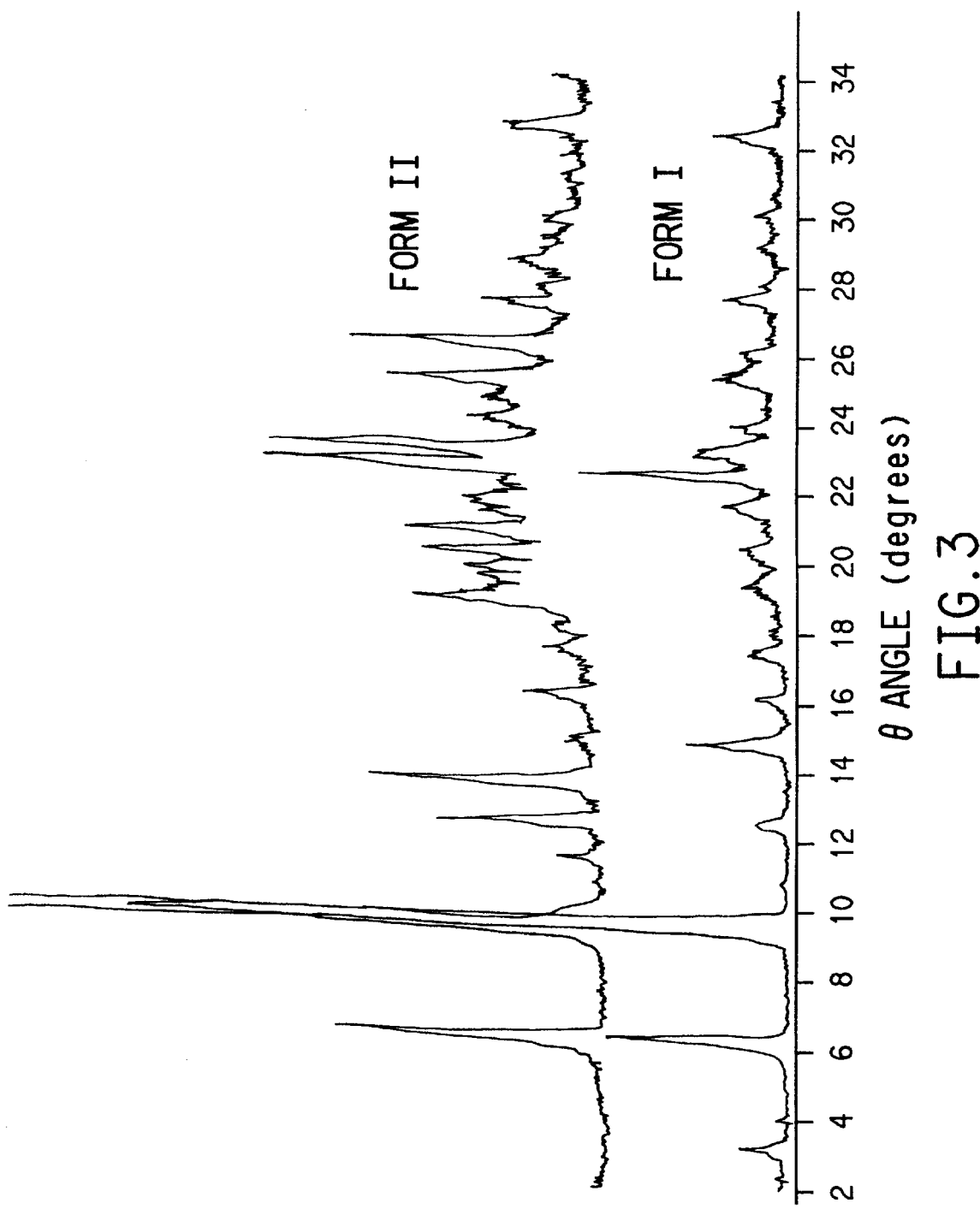
FIG. 3 shows powder x-ray diffractograms of the Form 1 and Form 2 crystalline polymorphs of roxifiban.

In another preferred embodiment, the Form 1 polymorph is characterized by an x-ray powder diffraction pattern substantially in accordance with that shown in FIG. 3.

In a second embodiment, the present invention describes a pharmaceutical composition prepared by combining a therapeutically effective amount of the Form 1 polymorph with a pharmaceutically acceptable carrier.

In a preferred embodiment, the pharmaceutical composition is in solid or liquid form.

In an even more preferred embodiment, the pharmaceutical composition contains from about 0.1 mg to about 25 mg of the compound per unit dose.

In a third embodiment, the present invention describes a pharmaceutical composition in solid unit dosage form which comprises a therapeutically effective amount of the Form 1 polymorph and a pharmaceutically acceptable carrier.

In a preferred embodiment, the pharmaceutical composition in capsule, tablet, powder or granule form and which contains from about 0.1 mg to about 25 mg of the compound.

In a fourth embodiment, the present invention describes a method for inhibiting the binding of a soluble adhesive protein to platelet glycoprotein IIb/IIIa complex which comprises providing the Form 1 polymorph, in an amount sufficient to result in the platelet glycoprotein IIb/IIIa complex being contacted with an effective inhibitory amount of the active drug substance.

In a preferred embodiment, the soluble adhesive protein is fibrinogen, von Willebrand factor, fibronectin or vitronectin.

In another preferred embodiment, the compound is provided to a human or animal subject to inhibit binding of a soluble adhesive protein to platelet glycoprotein IIb/IIIa complex in vivo.

In another preferred embodiment, the compound is provided to a blood-containing extracorporeal device to inhibit binding of a soluble adhesive protein to platelet glycoprotein IIb/IIIa complex in vitro.

In a fifth embodiment, the present invention describes a method for the treating or preventing thromoembolic disorders selected from thrombus or embolus formation, harmful platelet aggregation, reocclusion following thrombolysis, reperfusion injury, restenosis, artherosclerlosis, stroke, myocardial infarction and unstable angina, which comprises administering to a host in need of such treatment or prevention a therapeutically effective amount the Form 1 polymorph.

In a preferred embodiment, the compound is administered at a dosage from about 0.001 to about 10 mg/kg of body weight per day.

In another preferred embodiment, the compound is administered at a dosage from about 0.005 to about 1 mg/kg of body weight per day.

In a more preferred embodiment, the compound is administered for the treatment or prevention of myocardial infarction or stroke.

In a sixth embodiment, the present invention describes a method for treating or preventing rhumatoid arthritis, asthma, allergies, adult respiratory syndrome, organ transplatation rejection, septic shock, psoriasis, contact dermatitis, osteoporosis, osteoarthritis, tumor metastatis, diabetic retinopathy, inflammatory conditions and inflammatory bowel disease, comprising administering to a host in need of such treatment or prevention a therapeutically or prophylactically effective amount of the Form 1 polymorph.

In a seventh embodiment, the present invention describes the Form 1 polymorph of crystalline roxifiban prepared by recrystallization of roxifiban from a mixed solvent system.

In an eighth embodiment, the present invention provides the Form 2 polymorph of crystalline roxifiban in substantially pure form.

In a preferred embodiment, the Form 2 crystalline roxifiban is greater than 90 percent pure.

In another preferred embodiment, the Form 2 polymorph is characterized by a solid-state $^{13}$C CP/MAS NMR spectrum having a single peak at 66 ppm and no significant peak at 63 ppm.

In a more preferred embodiment, the solid-state 13C CP/MAS NMR spectrum of the Form 2 polymorph has a single peak at 19 ppm and no significant peak at 21 ppm.

Figure 2:
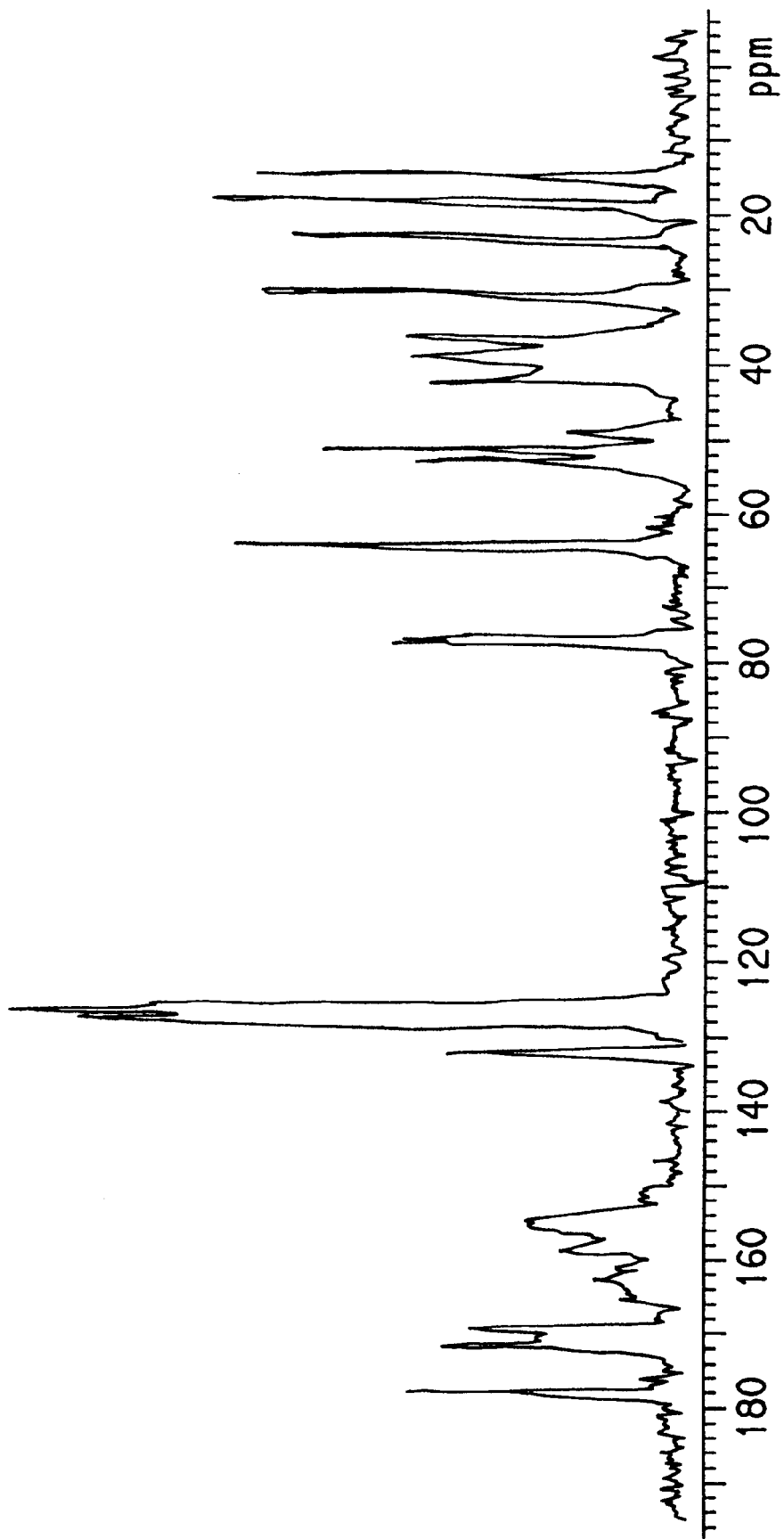
FIG. 2 is a solid-state $^{13}$C CP/MAS NMR spectrum of the Form 2 crystalline polymorph of roxifiban.

In another preferred embodiment, the Form 2 polymorph has a solid-state 13C CP/MAS NMR spectrum substantially in accordance with that shown in FIG. 2.

In another preferred embodiment, the Form 2 polymorph is characterized by an x-ray powder diffraction pattern comprising 2θ values of 6.4±0.2, 9.6±0.2, 12.4±0.2, 13.6±0.2, 18.8±0.2, 20.7±0.2, 22.6±0.2, 23.1±0.2, 25.1±0.2, 26.1±0.2, 27.3±0.2, and 28.5±0.2.

In another preferred embodiment, the Form 2 polymorph is characterized by an x-ray powder diffraction pattern substantially in accordance with that shown in FIG. 3.

In a ninth embodiment, the present invention describes a pharmaceutical composition prepared by combining a therapeutically effective amount of the Form 2 polymorph with a pharmaceutically acceptable carrier.

In a preferred embodiment, the pharmaceutical composition is in solid or liquid form.

In an even more preferred embodiment, the pharmaceutical composition contains from about 0.1 mg to about 25 mg of the compound per unit dose.

In a tenth embodiment, the present invention describes a pharmaceutical composition in solid unit dosage form which comprises a therapeutically effective amount of the Form 2 polymorph and a pharmaceutically acceptable carrier.

In a preferred embodiment, the pharmaceutical composition in capsule, tablet, powder or granule form and which contains from about 0.1 mg to about 25 mg of the compound.

In a eleventh embodiment, the present invention describes a method for inhibiting the binding of a soluble adhesive protein to platelet glycoprotein IIb/IIIa complex which comprises providing the Form 2 polymorph, in an amount sufficient to result in the platelet glycoprotein IIb/IIIa complex being contacted with an effective inhibitory amount of the active drug substance.

In a preferred embodiment, the soluble adhesive protein is fibrinogen, von Willebrand factor, fibronectin or vitronectin.

In another preferred embodiment, the compound is provided to a human or animal subject to inhibit binding of a soluble adhesive protein to platelet glycoprotein IIb/IIIa complex in vivo.

In another preferred embodiment, the compound is provided to a blood-containing extracorporeal device to inhibit binding of a soluble adhesive protein to platelet glycoprotein IIb/IIIa complex in vitro.

In a twelfth embodiment, the present invention describes a method for the treating or preventing thromoembolic disorders selected from thrombus or embolus formation, harmful platelet aggregation, reocclusion following thrombolysis, reperfusion injury, restenosis, artherosclerlosis, stroke, myocardial infarction and unstable angina, which comprises administering to a host in need of such treatment or prevention a therapeutically effective amount the Form 2 polymorph.

In a preferred embodiment, the compound is administered at a dosage from about 0.001 to about 10 mg/kg of body weight per day.

In another preferred embodiment, the compound is administered at a dosage from about 0.005 to about 1 mg/kg of body weight per day.

In a more preferred embodiment, the compound is administered for the treatment or prevention of myocardial infarction or stroke.

In a thirteenth embodiment, the present invention describes a method for treating or preventing rhumatoid arthritis, asthma, allergies, adult respiratory syndrome, organ transplatation rejection, septic shock, psoriasis, contact dermatitis, osteoporosis, osteoarthritis, tumor metastatis, diabetic retinopathy, inflammatory conditions and inflammatory bowel disease, comprising administering to a host in need of such treatment or prevention a therapeutically or prophylactically effective amount of the Form 1 polymorph.

In a fourteenth embodiment, the present invention describes the Form 2 polymorph of crystalline roxifiban prepared by recrystallization of roxifiban from a mixed solvent system.

Synthesis

Roxifiban is the acetate salt of the methyl ester prodrug of an optically pure enantiomer of a therapeutically active isoxazoline compound of the structure:

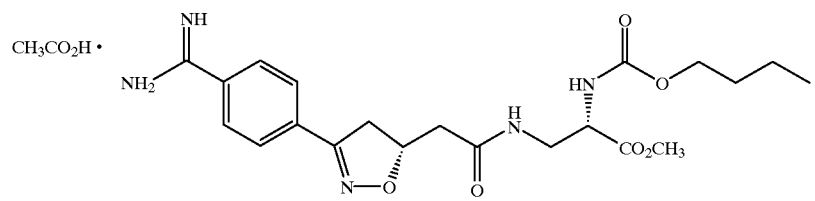

The synthesis of the trifluoroacetic acid salt of the methyl ester of active drug substance (II) is described in Example 314B of PCT/US94/13155. As will be appreciated by those skilled in organic chemical synthesis, the procedure described therein may adapted for the production of roxifiban by substituting acetic acid for trifluoroacetic acid in the final process step.

An alternative method for producing crystalline roxifiban is described in the above-referenced publications by Zhang et al. This synthesis begins with the reaction of 4-cyanobenzaldehyde with hydroxyamine sulfate to yield 4-cyanobenzaldoxime, using essentially the method described by Kawase and Kakugawa, J.Chem. Soc., Perkin Trans I, 1979, p. 643. The reaction is illustrated by the following equation:

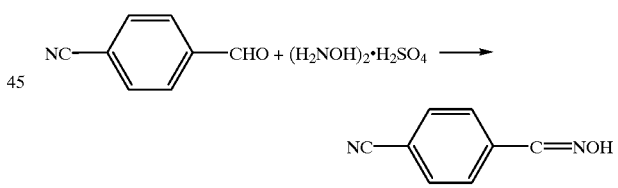

Reaction of the 4-cyanobenzaldoxime with N-chlorosuccinimide in the presence of triethylamine generates the active nitrile oxide intermediate, which further condenses with isobutyl vinylacetate to yield a racemic mixture of a compound represented by the formula:

(III)

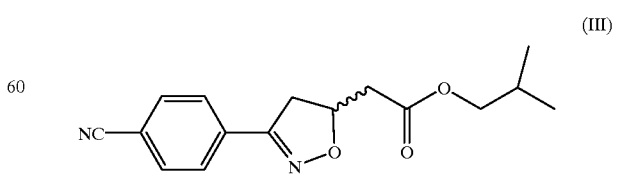

Enzymatic hydrolysis of the racemic mixture of compound III with a lipase produces an isoxazoline acid in the optically pure R configuration. This isoxazoline acid is represented by the formula:

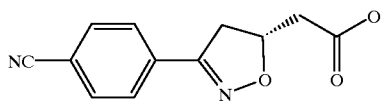

(IV)

The enzymatic reaction may be conducted using a commercially available lipase preparation, such as lipase PS30, available from Amano Enzyme. The reaction may be conducted in a pH 7.5 phosphate buffer.

Unhydrolyzed isobutyl ester of formula III having the S configuration may be racemized with a catalytic amount of potassium t-butoxide. By repetition of this enzymatic hydrolysis-base epimerization process, the optically pure isoxazoline acid may be recovered in good yield.

The optically pure isoxazoline acid of formula IV is coupled with the methyl ester of N-(-butoxycarbonyl-1,2-diaminopropionic acid to yield an optically pure intermediate of the formula:

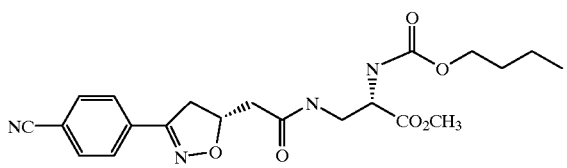

(V)

The optically pure amino acid N-(-butoxycarbonyl-1,2-diaminopropionic acid is commercially available (for example, from Bachem) and may be converted to its methyl ester by reaction with methanol in the presence of thionyl-chloride.

Compound V is converted to the imidate intermediate via Pinner reaction (Allen et al., *J. Am. Chem. Soc.* (1958) 80, 591; Zhang et al., *Tetrahedron Letters*, (1996) 37(26), 4455–58). The imidate intermediate may be reacted with ammonium acetate to yield the desired acetate salt, roxifiban (I) in good yield. Crystalline roxifiban may be recovered from the reaction medium and dried to yield crystalline roxifiban in good yield.

This procedure has been found to produce a mixture of two crystalline polymorphs of roxifiban, designated Form 1 and Form 2.

Recrystallization of roxifiban from dilute solutions in methanol yields the Form 1 polymorph. The recrystallization solution advantageously contains greater than about 20 mL of methanol per gram of roxifiban, preferably greater than about 25 mL of methanol per gram of roxifiban. At higher concentrations of roxifiban, recrystallization from methanol often yields mixtures of the Form 1 and Form 2 polymorphs. The production of the Form 1 polymorph is favored by relatively rapid cooling of the methanol solution. Advantageously, a dilute methanol solution of roxifiban is heated to a temperature of from about 50° C. to about 65° C. to effect complete dissolution of the compound. This solution is then cooled to <35° C. to cause crystallization of a product that is predominantly Form 1.

The Form 1 polymorph may also be produced by the addition of anti-solvents, such as methylacetate, to dilute methanol solutions of the compound.

Alternatively, the addition of hot xylene to heated solutions of roxifiban in methanol, followed by rapid distillation of methanol from the solution, yields a crystalline product that is predominantly the Form 1 polymorph. A procedure that has been found to yield the Form 1 crystalline polymorph of roxifiban in substantially pure form is described in Example 2 below.

The production of the Form 2 polymorph is favored by relatively slow cooling of recrystallization solution. Advantageously, a solution containing less than about 20 mL of solvent per gram of roxifiban, preferably less than about 10 mL of solvent per gram of roxifiban is heated to a temperature of from about 50° C. to about 65° C. to effect complete dissolution of the compound. This solution is then cooled to <35° C. to cause crystallization of a product that is predominantly Form 2.

The Form 2 polymorph may be recovered in good yield and high purity by slow cooling of concentrated solutions of roxifiban in a methanol-acetic acid-acetonitrile mixed solvent. A preferred mixed solvent system contains methanol-acetic acid-acetonitrile in a volume ratio of about 10:1.5:10.

The Form 1 and Form 2 polymorphs of crystalline roxifiban may be readily distinguished by X-ray powder diffraction and solid-state carbon NMR. The X-ray diffractograms of the Form 1 and Form 2 polymorphs are shown in FIG. 3. The main peaks in the diffractogram for the Form 1 polymorph occur at 2θ values of about 6.4, 9.6, 12.5, 14.7, 19.3, 21.5, 22.5, 23.2, 25.2, 27.5, and 32.2. The relative intensities of the peaks may vary, depending upon the sample preparation technique, the sample mounting procedure and the particular instrument employed. Moreover, instrument variation and other factors may affect the 2θ values, therefore, the peak assignments may vary by plus or minus 0.2.

The region of the diffractogram that is most useful in distinguishing the Form 1 and Form 2 polymorphs occurs in the region of about 13.6°. The Form 2 polymorph exhibits a strong peak at this angle, while the diffractogram of the Form 1 polymorph is substantially flat in this region.

Analysis by solid state carbon NMR is also a useful procedure for polymorphic characterization of crystalline roxifiban. The solid-state $^{13}C$ NMR spectra, using the CP/MAS technique, confirm the existence of the Form 1 and Form 2 polymorphs of roxifiban. As shown in the spectrum in FIG. 1, the Form 1 polymorph has a lower-symmetry structure, as evidenced by the occupation of the n-butyl group in one of two crystallographically-inequivalent positions. In contrast, as shown in the spectrum in FIG. 2, the n-butyl group of the Form 2 polymorph resides in a single defined structural location. Thus, the spectrum of the Form 1 polymorph is characterized by doublet peaks at 63 and 66 ppm and at 19 and 21 ppm. The spectrum of the Form 2 polymorph exhibits single peaks at 66 and 19 ppm.

Figure 4:
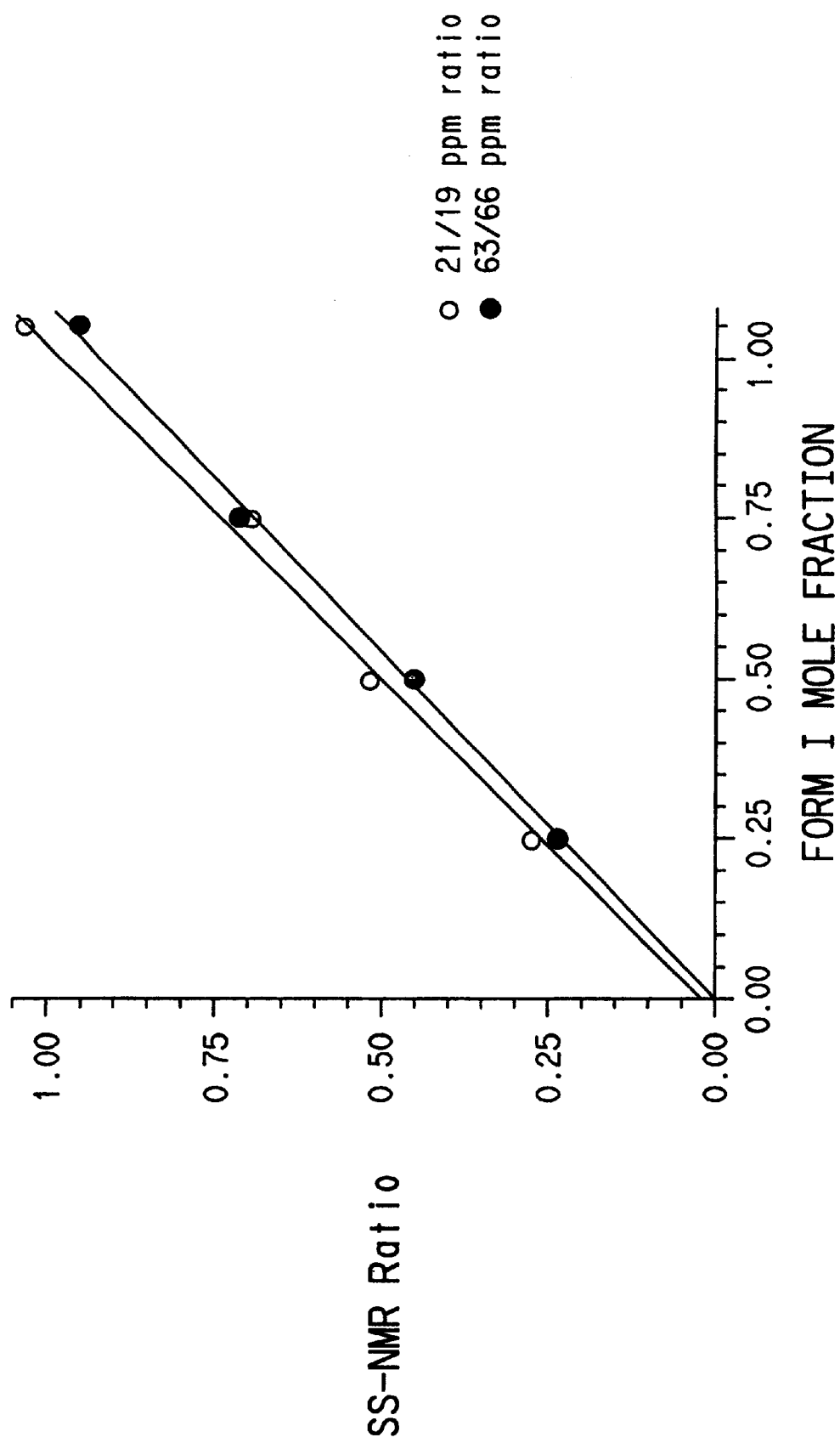
FIG. 4 is a standard curve plotting peak area ratios of the $^{13}$C CP/MAS NMR spectra of mixtures of the Form 1 and Form 2 polymorphs of roxifiban against the molar proportion of the Form 1 polymorph in such mixture.

The solid-state $^{13}C$ NMR procedure can be used for quantitative analysis of mixtures of the Form 1 and Form 2 polymorphs. The ratio of the area of the peak at 63 ppm to the area of the peak at 66 ppm correlates well with the molar ratio of the Form 1 to Form 2 polymorphs. In addition, the ratio of the area of the peak at 21 ppm to the area of the peak at 19 ppm also correlates well to the Form 1:Form 2 molar ratio. A standard curve prepared by regression analysis of ratios obtained from mixtures of the polymorphs can be prepared and utilized for analysis. Such a calibration curve is illustrated in FIG. 4 of the drawings.

While the solid-state carbon NMR procedure may be used for quantitative analysis of polymorphic mixtures, the invention is not restricted to any particular method of analysis for or identification of the desired polymorph.

Isothermal microcalorimetry and phase solubility studies have revealed that the thermodynamic stabilities of the two forms of roxifiban are very similar. The Form 2 polymorph is believed to be more stable at temperatures below about 132° C., while the Form 1 polymorph is slightly more stable at temperatures above 132° C. These differences are minor, and the Form 1 product is polymorphically stable following storage for 19 months at room temperature. Spontaneous conversion of the Form 1 polymorph to the Form 2 polymorph has not been observed. The aqueous solubilities of the Form 1 and Form 2 crystalline polymorphs of roxifiban are very close, and biological differences of the two polymorphic forms have not been observed.

Unit cell parameters and atomic coordinates of the Form 1 and Form 2 crystalline polymorphs can be determined by single-crystal x-ray diffraction techniques if suitably large crystals are available. If Forms 1 and 2 of Roxifiban grow needle or plate crystals, they may never achieve a large enough volume for single diffraction patterns. Generally, analysis of the two forms in single crystal studies show that the crystals are twinned or agglomerated. In this case, transmission electron microscopy (TEM) and synchrotron x-ray powder diffraction may be employed to determine the unit cells.

Definitions

The term "mixed solvent system" as used herein refers to a solvent system comprising a mixture of two or more solvents. Preferred mixed solvent systems in the present invention are mixed solvent systems comprising acetic acid, acetonitrile and acetone or acetic acid, anisole and acetone.

The present invention describes polymorphs in substantially pure form. As used herein, "substantially pure" means a compound having a purity greater than 90 percent, including 90, 91, 92, 93, 94, 95, 96, 97, 98, 99, and 100 percent.

The crystalline forms of roxifiban described herein may be formulated into pharmaceutical compositions and employed in therapeutic and prophylactic methods as described in the aforementioned International Patent Application Number PCT\US94\13155. For example, in addition to their use in the treatment of the thromboembolic disorders and other cell-adhesion related diseases referred to above, the novel crystalline roxifiban products of this invention may be utilized in surgery on peripheral arteries (arterial grafts, carotid endarterectomy and in cardiovascular surgery where manipulation of arteries and organs and/or the interaction of platelets with artificial surfaces leads to platelet aggregation and consumption, and where the aggregated platelets may form thrombi and thromboemboli. Formulations containing the compounds of this invention may be administered to surgical patients to prevent the formation of thrombi and thromboemboli.

Such crystalline compounds may also be used in extracorporeal devices to inhibit the interaction of the platelet glycoprotein IIb/IIIa on platelet membranes with fibrinogen or other cell adhesion proteins absorbed to the surface of the extracorporeal circuit.

The crystalline forms of roxifiban of this invention may be administered in oral dosage forms such as tablets, capsules (each of which includes sustained release or timed release formulations), pills, powders, granules, elixirs, tinctures, suspensions, syrups, and emulsions. Likewise, they may also be administered in intraveneous (bolus or infusion), intraperitoneal, subcutaneous or intramuscular forms or by transdermal iontophoretic delivery, all using dosage forms well known to those of ordinary skill in the pharmaceutical arts.

When dissolved, roxifiban loses its crystalline structure; however it may be used for the preparation of liquid formulations in which the drug is dissolved or suspended. In addition, the crystalline roxifiban may be incorporated into solid formulations such as tablets, capsules, suspensions and the like. A therapeutically effective amount of the crystalline roxifiban is combined with a pharmaceutically acceptable carrier to produce the pharmaceutical compositions of this invention. By "therapeutically effective amount" it is meant an amount that, when administered alone or with an additional therapeutic agent, is effective to prevent or ameliorate the disease or condition or the progression of the disease or condition.

Dosage forms (pharmaceutical compositions) suitable for administration may generally contain from about 0.05 mg to about 50 mg of crystalline roxifiban per dosage unit. In these pharmaceutical compositions, the crystalline roxifiban would ordinarily be present in an amount of from about 0.1–95% by weight based on the total weight of the composition.

For oral administration in the form of a tablet or capsule, the crystalline roxifiban can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like. For oral administration in liquid form, the crystalline roxifiban can be combined with any oral, non-toxic pharmaceutically acceptable inert carrier such as ethanol, glycerol, water and the like. When desired or necessary, suitable binders, lubricants, disintegrating agents, flavorants and coloring agents can also be incorporated. Suitable binders include starch, gelatin, natural sugars, glucose or beta-lactose, corn sweetners, natural and synthetic gums such as acacia, tragacanth or sodium alginate, carboxymethylcellulose, polyethylene glycol, waxes and the like. Lubricants used in these dosages include sodium oleate, sodium stearate, magnesium stearate, sodium benzoate, sodium acetate, sodium chloride and the like. Disintegrators include, without limitation, starch, methylcellulose, agar, bentonite, xanthan gum, and the like.

The crystalline roxifiban compounds of this invention can also be formulated into compositions for intranasal or topical use, using delivery systems well known to those skilled in the art. Alternatively, transdermal iontophoretic skin patches may be employed for continuous delivery of the drug.

The crystalline roxifiban can also be administered from liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Crystalline roxifiban may also be coupled with soluble polymers as targetable drug carriers. Such polymers can include polyvinylpyrrolidine pyran copolymer, polyhydroxypropylmethacrylamide-phenol, polyhydroxyethylaspartamidephenol or polyethylene oxide-polylysine substituted with palmitolyl residues. Furthermore, the crystalline roxifiban may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of crystalline roxifiban may contain the compound and powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track. In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline roxifiban in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chluoride, methyl- or propyl-paraben and chlorobutanol.

Suitable pharmaceutical carriers are described in Remington's Pharmaceutical Sciences, Mack Publishing Co., a standard reference text in this field.

Representative useful pharmaceutical dosage-forms for administration of the crystalline roxifiban of this invention may be illustrated as follows:

Capsules

A large number of unit capsules are prepared by filling standard two-piece hard gelatin capsules each with 2 milligrams of crystalline roxifiban, 150 milligrams of lactose, 50 milligrams of cellulose, and 6 milligrams magnesium stearate.

Soft Gelatin Capsules

A mixture of crystalline roxifiban in a digestable oil such as soybean oil, cottonseed oil or olive oil is prepared and injected by means of a positive displacement pump into gelatin to form soft gelatin capsules containing 2 milligrams of roxifiban. The capsules are washed and dried.

Tablets

A large number of tablets are prepared by conventional procedures so that the dosage unit was 2 milligrams of crystalline roxifiban, 0.2 milligrams of colloidal silicon dioxide, 5 milligrams of magnesium stearate, 275 milligrams of microcrystalline cellulose, 11 milligrams of starch ad 98.8 milligrams of lactose. Appriopriate coatings may be applied to increase palatability or delay absorption.

Injectable

A parenteral composition suitable for administration by injection is prepared by stirring 0.2% by weight of crystalline roxifiban in 10% by volume propylene glycol and water. The solution is made isotonic with sodium chloride and sterilized.

Suspension

An aqueous suspension is prepared for oral administration so that each 5 mL contains 2 mg of finely divided crystalline roxifiban, 200 mg of sodium carboxymethyl cellulose, 5 mg of sodium benzoate, 1.0 g of sorbitol solution, U.S.P., and 0.025 mL of vanillin.

Analytical Methods

X-Ray Powder Diffraction

X-ray powder diffraction data were obtained with a Philips Model 3720 automated powder diffractometer. Samples were run in a batch mode with a Model PW 1775 multi-position sample changer. The diffractometer was equipped with a variable slit (θ-compensating slit), a scintillation counter and a graphite monochromator. The radiation was CuKα (40 kV, 30 mA). Data were collected at room temperature from 2 to 60 degrees 2°; the step size was 0.02 degrees; the count time was 0.5 sec. per step. Samples were prepared on glass specimen holders as a thin layer of powdered mateiral without solvent.

Solid-State Carbon NMR

Solid-state $^{13}$C NMR spectra were acquired on a Varian VXR-200S NMR operating at 50.3 MHz for $^{13}$C using the CP/MAS technique. Approximately 200 mg of sample was used in the acquisition of the spectra. All measurements were made at ambient temperature. Chemical shifts were reported on the TMS scale using hexamethylbenzene as a secondary reference. Solid-state resonance assignments were made using the interrupted decoupling pulse sequence in combination with solution-state $^{13}$C experiments performed on a Varian Unity 400 NMR operating at 100 MHz.

A positive assignment of the origin of signal multiplicities in the spectra required additional $^{13}$C CP/MAS NMR experiments to be performed at a lower static field strength. This was done on a 100-MHz spectrometer with a $^{13}$C resonance frequency of 25.2 MHz.

Synchrotron X-Ray Powder Diffraction

The unit cell parameters of two polymorphs of Roxifiban were determined by a combination of transmission electron microscopy (TEM) and synchrotron x-ray powder diffraction. TEM employed a JEM-2000EX (at 200 kV accelerated voltage) microscope, equipped with a Gatan 1024×1024 CCD camera to characterize the materials. Synchrotron x-ray powder diffraction patterns were collected on a Huber diffractometer at beamline DND-5BMB. A Si(111) analyzer, and slits on the order of 1×8 mm were used in conduction with a scintillation counter to achieve the highest possible resolution and signal/noise ratio.

EXAMPLES

The invention is further illustrated by the following examples, which are not intended to limit the invention.

Example 1

Synthesis of Crystalline Roxifiban

4-Cyanobenzaldoxime.

A solution of methanol (272.1 L) 4-cyanobenzaldehyde (50 kg, 381.3 mol), and hydroxylamine sulfate (36.1 kg. 219.7 mol) was stirred at 55–60° C. for 3 h, and then water (272 L) was added. The mixture was cooled to 0–5° C. and held for 30 min. The crude product was collected by filtration. The filter cake was washed with a mixed solvent of cold methanol and water (2/3 ratio, 735.0 L) and water (750.0 L) and dried under vacuum (60–70° C.) to constant weight: 54.1 kg, 97% yield; mp 174–6° C.; $^1$H NMR ∂ 7.82 (2H), 7.88 (2H), 88.26 (1H), 12.00 (1H). Anal. Calcd for $C_8H_6N_2O$: C, 65.75; H, 4.14; N, 19.17. Found C, 65.73; H, 4.26; N, 19.14.

(−)-Isobutyl 2-[3-(4-Cyanophenyl)-4,5-dihydro-5-isoxazolyl]acetate (III).

To a solution of DMF (262.0 L), 4-cyanobenzaldoxime (46 kg, 342.1 mol), and N-chlorosuccinimide (54 kg, 389.4 mol) was added isobutyl vinylacetate (95 kg. 665.7 mol). The solution was cooled to 2–6° C., and triethylamine (40 kg. 388.6 mol) was slowly added over a period of 4 h. The reaction was stirred at the same temperature for an addition 1 h. Water (330.0 L) and hydrochloric acid (1 N, 49 L) were added. The crude product was collected by filtration, washed with water (555.0 L), and redissolved in toluene (500.0 L, 40° C.). The organic layer was washed with water (291.0 L) and dried by azeotropic distillation (removing about 250 L of toluene). Heptane (300.0 L) was added, and the reaction was cooled at 0–5° C. for 3 h. The product was collected by filtration and washed with toluene/heptane (150.0 L, 1/2 ratio). The product was dried under vacuum at 55–60° C. to constant weight: 81.8 kg, 90% yield, mp 98–100° C.; $^1$H NMR (CDCl$_3$) ∂ 0.96 (6H), 1.96 (1H), 2.70 (1H), 2.92 (1H), 3.15 (1H), 3.56 (1H), 3.90 (2H), 5.20 (1H), 7.70 (2H), 7.80 (2H). Anal. Calcd. for $C_{16}H_{18}N_2O_3$: C, 67.12; H, 6.34; N. 9.78. Found: C, 67.06; H, 6.20; N, 9.76.

(R)-2-[3-(4-Cynnophenyl)-4,5-dihydro-5-isoxazolyl] acetic Acid.

A suspension of H$_2$O (597.0 L), NaH$_2$PO$_4$—H$_2$O (60.0 kg), aqueous NaOH (33%, 36.0 L), Triton X-100 (3.2 kg), compound III (40.0 Kg, 139.7 mol), and lipase PS30 (4.0 kg, enzyme content 8%) was slowly heated to 40° C. and held in the temperature range of 40–43° C. until the resolution was completed (~16 h) The pH of the reaction mixture was maintained between 7.4 and 8.0 and adjusted by the addition of 33% aqueous NaOH. The batch was cooled to 20–25° C. when the reaction was completed, and the pH of the reaction mixture was adjusted to between 8.0 and 8.2 by the addition of aqueous NaOH (33%, 11.0 L). The crude unreacted s-ester was collected by a filtration through a layer of Celite (20 kg) and washed with water (70 L). The crude ester was recycled through a racemization step: $^1$H NMR (CDCl$_3$) ∂ 0.95 (6H), 1.8 (1H), 2.69 (1H), 2.91 (1H), 3.14 (1H), 3.54 (1H), 3.91 (2H), 5.13–5.23 (1H), 7.68–7.78 (4H).

The pH of the solution of filtrate (~800 L) and isopropyl acetate (20 L) was adjusted to 2.8–3.2 with concentrated hydrochloric acid (~57 kg). The crude product acid IV was precipitated, collected by filtration, and washed with water (70 L). This crude product was crystallized from hot ethanol (525.0 L) to give optically pure IV. Isoxazoline IV was collected by filtration, washed with ethanol (76.0 L), and dried to constant weight: 12.3 kg, 77% yield based on the amount of a IV in III; mp 198–200° C.; $^1$H NMR ∂ 2.70 (2H), 3.20 (1H), 3.59 (1H), 5.00–5.10 (1H), 7.78–7.91 (4H), 12.44 (1H). Anal. Calcd. for $C_{12}H_{10}N_2O_3$: C, 62.61; H, 4.38; N, 12.17. Found: C, 62.39; H, 4.49; N, 11.98.

Racemization of S-ester to III.

A solution of toluene (414.0 L) and crude s-ester (~120 kg wet cake) was heated to 50° C. and filtered to remove Celite (~40 kg). The filter cake was washed by toluene (72.0 L). The organic layers were combined and washed by brine (108.0 L). After removal of the aqueous layer, the organic layer was dried by azeotropic distillation to constant boiling point (111° C.). The batch was cooled to 40° C., and potassium tert-butoxide in tert-butyl alcohol (1 N, 1.6 L) was added. The reaction was agitated (200 rpm) at 40° C. until racemization was completed. The batch was cooled to 20–25° C., and water (108.0 L) was added. The reaction mixture was neutralized by the addition of aqueous hydrochloric acid (1 N, 1.6 L). The aqueous bottom layer was removed, and the organic layer was concentrated by distillation. The reaction was cooled to 60° C. when ~380.0 L of toluene was removed. To this solution was added heptane (115 L), and the reaction was held at 50° C. for 1 h. The mixture was cooled to 0–5° C. and held for 2 h. The product IV was collected by filtration and washed with a mixed solvent of toluene and heptane (1/2 ratio, 70 L). The product III was dried under vacuum (50–55° C.) to constant weight: 17.3 kg., 87% yield.

(R)-Methyl-3-[[[3-(4-cyanophenyl)-4,5-dihydro-5-isoxazolyl]acetyl]amino]-N-(butoxycarbonyl)-L-alanine (V).

A solution of acetonitrile (402.0 L), acid IV (12.0 kg, 52.10 mol), amine (22.4 kg, 57.30 mol), and thionyl chloride (6.8 kg, 57.30 mol) was stirred at 0–5° C. for 1 h. To this solution was added diisopropylethylamine (22.2 kg, 172.00 mol) at 20° C over a period of 90 min. Water (612.0 L) was added after the reaction. The crude product V precipitated out. This crude V was collected by filtration and washed with water (96.0 L). The wet cake was dissolved in hot methanol (50–60° C., 311.0 L), and any insoluble particles were removed by filtration. The solution was cooled at 0–5° C. for 3 h, and the product was collected by filtration and washed with methanol (75.0 L). The product was dried under vacuum (55–60° C.) to constant weight: 18.3 kg, 82% yield, mp 154–6° C.; $^1$H NMR ∂ 0.92 (3H), 1.37 (2H), 1.59 (2H), 1.67 (1H), 2.58 (1H), 2.71 (1H), 3.22 (1H), 3.51 (1H), 3.67 (2H), 3.77 (3H), 4.06 (2H), 4.44 (1H), 5.14 (1H), 5.70 (1H), 6.38 (1H), 7.70 (2H), 7.77 (2H). Anal. Calcd for $C_{12}H_{10}N_2O_6$; C, 62.61; H, 4.38; N, 12.17. Found C, 62.39; H, 4.49; N, 11.98.

(R)-methyl-3-[[[3-[4-(aminoiminomethyl)phenyl]-4,5-dihydro-5-isoxazolyl]acetyl]amino]-N-(butoxycarbonyl)-L-alanine Monoacetate (I).

A solution of methyl acetate (55.8 L), methanol (4.8 L), HCL (9.6 kg), and compound 4 (12.0 kg., 27.88 mol) was cooled to −20° C. and stirred under 3–5 psi (HCl) at 10° C. for 27 h. After the reaction, the HCl was removed under vacuum, and the methyl acetate (21.5 L) and methanol (63.2 L) were added. The residual HCl was neutralized with ammonia (2.5 kg) under 10° C. The resulting ammonium chloride was removed by filtration. The filter cake was washed by methyl acetate and methanol (20.0 L). To the filtrate was added ammonium acetate (6 kg), and the reaction was stirred at room temperature overnight. The crude product was collected by filtration to give DMP 754: 10.4 kg, 74% yield.

Example 2

Form 1 Polymorph of Crystalline Roxifiban

A slurry of roxifiban (1.38 kg, 2.73 moles) in acetonitrile (5.5 L) was added to glacial acetic acid (2.77 L, 48.4 moles). This slurry was heated to 80° C. and all solids dissolved. The solution was then cooled to 40–45° C. and acetone (12.5 L) was added over 30 minutes. The resulting slurry was stirred at 20–25° C. for one hour, then cooled to 0–5° C. for one hour. The solids were filtered, rinsed with a 10% methanol-acetone solution (11 L), and dried in vacuo at 65° C. This procedure yielded 1.26 kg (91%) of the Form 1 polymorph of crystalline roxifiban.

Powder x-ray diffraction analysis of this material was performed as described above. The diffractogram is shown in FIG. 3. The diffractogram exhibits 2θ values of 6.4±0.2, 9.6±0.2, 12.5±0.2, 14.7±0.2, 19.3±0.2, 21.5±0.2, 22.5±0.2, 23.2±0.2, 25.2±0.2, 27.5±0.2, and 32.2±0.2. Solid state $^{13}$C CP/MAS NMR analysis was also performed as described above. The resulting spectrum is shown in FIG. 1. The spectrum exhibits doublet peaks at 19/21 ppm and 63/66 ppm, which are characteristic of the Form 1 polymorph. This material was determined to be substantially pure Form 1 polymorph of roxifiban, with no detectable Form 2 polymorph.

Example 3

A solution of roxifiban (2.0 g, 3.9 mmol) was prepared by dissolution into methanol (15 mL) and acetic acid (3 mL) at reflux. Any insolubles were removed by filtration through Celite; any roxifiban that crystallized on the filter particles was washed through with a wash of 5 mL of warm methanol. The filtrate was reheated to reflux and once all solids had dissolved, acetonitrile (20 mL) was added over 10 min. The solution was heated another 10 min to redissolve any solids that may have appeared during the acetonitrile addition and cooled slowly to ambient temperature over 2 hr. Once cooling was initiated, the solution was seeded with traces of Form 2 crystals until a haziness persists in suspension. After 2 hr, the suspension was reheated to reflux and 30 mL of distillate was removed while maintaining the volume with acetonitrile. The volume was further diluted with another 8 mL acetonitrile and the slurry cooled to 15° C. over 100 min. The crystals were filtered, washed with 15 mL acetonitrile and dried under vacuum to yield roxifiban (1.82 g, 91% recovery) as white solids. By powder diffraction X-ray analysis, this was determined to be Form 2 and trace or no Form 1.

Example 4

The recrystallization was run in a manner similar to that of Example 3 except once the solvent exchange was complete, reflux was maintained overnight. Workup subsequently continued as for Example 3 to isolate roxifiban (1.83 g, 91% recovery) as white solids. By powder diffraction X-ray analysis, this was determined to be Form 2 and trace or no Form 1.

Example 5

To a 100 ml round bottom flask was added roxifiban Form 1 (3.6 g 6.1 mmol), 30 mL of methanol and ammonium acetate (0.47 g 6.1 mmol). The mixture was heated to reflux gently with vigorous stirring and the suspension was stirred at reflux for 6 hr. The mixture was then cooled slowly to ambient temperature over 4 hr. The solids were filtered and washed with 20 mL of solvent mixture of methanol and acetonitrile (1/1, v/v). The solids were dried under vacuum to yield roxifiban (3.1 g, 86% recovery) of white needles. By powder diffraction X-ray analysis, this was determined to be Form 2 and trace or no Form 1.

Example 6

To a 3 L round bottom flask was added roxifiban (108.0 g, 0.182 mmol, Form 1 and Form 2 mixture), ammonium acetate (15.2 g, 0.182 mmol) and 1100 mL of methanol. The mixture was heated to reflux and the resulting suspension was stirred for 4 hr. The mixture was then cooled to 10° C. over 5 hr. The solids were collected and washed with 400 mL solvent mixture of methanol and acetonitrile (1,1, v/v). The solids were dried under vacuum to give roxifiban (101.0 g, 93.5% recovery) of white needles of 99.9 area % and 100.6 wt % purity as determined by HPLC. By powder diffraction X-ray analysis, this product was determined to be Form 2 roxifiban and trace or no Form 1.

Example 7

Synchrotron powder diffractions were collected on samples of Form 1 and 2 of Roxifiban in order to determine the unit cell parameters of the two forms. Nine runs were performed using identical optics: Si(111)monochromator crystals, a Si(111)analyzing crystal, and a Soller slit. Two wavelengths, 0.49617 Å and 1.00006 Å, were employed. The samples were prepared as follows:

| Sample Preparation | wavelength |
| --- | --- |
| Form 1 in a 1.0 mm capillary | 0.49617 Å |
| Form 1 in a 1.5 mm capillary | " |
| Form 2 in a 1.0 mm capillary | " |
| Form 2 in a 1.5 mm capillary | " |
| Form 1 mounted unground as deep flat plate | 1.00006 Å |
| Form 1 mounted ground as deep flat plate | " |
| Form 2 mounted unground as deep flat plate | " |
| Form 2 mounted ground as deep flat plate | " |
| Form 1 and 2 mounted ground as deep flat plate | " |

Determination of Form 1 unit cell:

Transmission electron microscopy (TEM) suggested that the Form 1 cell was of low symmetry, either monoclinic or triclinic, with two of the three cell axes being about 5 and 9–10 Å, and angle of 81°. Synchrotron patterns showed the third axis was much longer (about ca. 27–28 Å). The volume per molecule is about 648 Å$^3$ which is compatible with two molecules per cell. The cell parameters were refined with CELLREF, and the numbers were used in a LeBail fit routine in GSAS. The refined triclinic unit cell parameters, with space group P1 and Z=2, provided the final unit cell determined for the Form 1 polymorph.

| FORM 1 | a | b | c | $\alpha$ | $\beta$ |
| --- | --- | --- | --- | --- | --- |
| Value: | 5.02349 | 28.07480 | 9.29536 | 98.533 | 98.498 |
| Sigma: | 0.00047 | 0.00228 | 0.00092 | 0.006 | 0.009 |
| | $\gamma$ | V | | | |
| Value: | 92.244 | 1279.712 | | | |
| Sigma: | 0.008 | 0.208 | | | |

Determination of Form 2 unit cell:

Transmission electron microscopy (TEM) results indicated that a, c and $\beta$, values of Form 1 and 2 are similar. The peaks in the Form 2 pattern could not be indexed unless one of the cell edges was doubled. This required that four molecules reside in the cell, and as such, the cell would likely be monoclinic, with a space group P21. The long axis was assumed to be b, because the TEM diffraction pattern suggested that 5–9 Å projection had a 81° angle. Adjusting the alpha and gamma angles to 90°, while adjusting the a, c, and $\beta$ angles gave a cell consistent with the Form 2 pattern. The cell parameters were refined with CELLREF, and the numbers were used in a LeBail fit routine in GSAS to determine the final unit cell for the Form 2 polymorph.

| FORM 2 | a | b | c | $\alpha$ | $\beta$ |
| --- | --- | --- | --- | --- | --- |
| Value: | 4.99190 | 54.77106 | 9.37211 | 90.000 | 99.154 |
| Sigma: | 0.00175 | 0.02405 | 0.00325 | 0.000 | 0.037 |
| | $\gamma$ | V | | | |
| Value: | 90.000 | 2529.806 | | | |
| Sigma: | 0.000 | 1.461 | | | |

What is claimed is:

1. The Form 1 polymorph of crystalline methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt having a solid state $^{13}$C CP/MAS NMR spectrum substantially in accordance with that shown in FIG. 1.

2. The Form 1 polymorph of claim 1, which has an x-ray powder diffraction pattern having four or more 2θ values selected from the group consisting of: 6.4±0.2, 9.6±0.2, 12.5±0.2, 14.7±0.2, 19.3±0.2, 21.5±0.2, 22.5±0.2, 23.2±0.2, 25.2±0.2, 27.5±0.2, and 32.2±0.2.

3. A pharmaceutical composition comprising a therapeutically effective amount of the compound of claim 1 and a pharmaceutically acceptable carrier.

4. The pharmaceutical composition of claim 3 which is in solid or liquid form and which contains from about 0.1 mg to about 25 mg of the compound per dose.

5. A method for inhibiting the binding of a soluble adhesive protein to platelet glycoprotein IIb/IIIa complex in a human or an animal which comprises administering to the human or animal in need thereof the compound of claim 2, in an amount sufficient to inhibit the binding of the soluble adhesive protein to the platelet glycoprotein IIb/IIIa complex.

6. A method for the treating or preventing throm/oembolic disorders selected from thrombus or embolus formation, harmful platelet aggregation, reocclusion following thrombolysis, reperfusion injury, restenosis, artherosclerlosis, stroke, myocardial infarction and unstable angina, which comprises administering to a host in need of thereof, a therapeutically effective amount of a compound of claim 1.

7. The method of claim 6, wherein the compound is administered at a dosage from about 0.001 to about 10 mg/kg of body weight per day.

8. The Form 1 polymorph of crystalline methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt prepared by recrystallization of methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt from a mixed solvent system.

9. The Form 2 polymorph of crystalline methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt having a solid-state $^{13}$C CP/MAS NMR spectrum substantially in accordance with that shown in FIG. 2.

10. The Form 2 polymorph of claim 9, which has an x-ray powder diffraction pattern having four or more 2θ values selected from the group consisting of: 6.4±0.2, 9.6±0.2, 12.4±0.2, 13.6±0.2, 18.8±0.2, 20.7±0.2, 22.6±0.2, 23.1±0.2, 25.1±0.2, 26.1±0.2, 27.3±0.2, and 28.5±0.2.

11. A pharmaceutical composition comprising a therapeutically effective amount of the compound of claim 9 and a pharmaceutically acceptable carrier.

12. The pharmaceutical composition of claim 11 which is in solid or liquid form and which contains from about 0.1 mg to about 25 mg of the compound per dose.

13. A method for inhibiting the binding of a soluble adhesive protein to platelet glycoprotein IIb/IIIa complex in a human or an animal which comprises administering to the human or animal in need thereof the compound of claim 9 in an amount sufficient to inhibit the binding of the soluble adhesive protein to the platelet glycoprotein IIb/IIIa complex.

14. A method for the treating or preventing thromoembolic disorders selected from thrombus or embolus formation, harmful platelet aggregation, reocclusion following thrombolysis, reperfusion injury, restenosis, artherosclerlosis, stroke, myocardial infarction and unstable angina, which comprises administering to a host in need thereof, a therapeutically effective amount of a compound of claim 9.

15. The method of claim 14, wherein the compound is administered at a dosage from about 0.001 to about 10 mg/kg of body weight per day.

16. The Form 2 polymorph of crystalline methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt prepared by recrystallization of methyl-$N^3$-[2-{3-(4-formamidinophenyl)-isoxazolin-5(R)-yl}-acetyl]-$N^2$-(n-butyloxycarbonyl)-2,3-(S)-diaminopropionate acetate salt from a mixed solvent system.

17. The Form 1 polymorph of crystalline methyl-$N^3$-[2-{3-(4-formamidinophenyl)-isoxazolin-5(R)-yl}-acetyl]-$N^2$-(n-butyloxycarbonyl)-2,3-(S)-diaminopropionate which has an x-ray powder diffraction pattern having four or more 2θ values selected from the group consisting of: 6.4±0.2, 9.6±0.2, 12.5±0.2, 14.7±0.2, 19.3±0.2, 21.5±0.2, 22.5±0.2, 23.2±0.2, 25.2±0.2, 27.5±0.2, and 32.2±0.2.

18. A pharmaceutical composition comprising a therapeutically effective amount of the compound of claim 17 and a pharmaceutically acceptable carrier.

19. The pharmaceutical composition of claim 18 which is in solid or liquid form and which contains from about 0.1 mg to about 25 mg of the compound per dose.

20. A method for inhibiting the binding of a soluble adhesive protein to platelet glycoprotein IIb/IIIa complex in a human or an animal, which comprises administering to the human or animal in need thereof the compound of claim 17, in an amount sufficient to inhibit the binding of the soluble adhesive protein to the platelet glycoprotein IIb/IIIa complex.

21. A method for the treating or preventing thromoembolic disorders selected from thrombus or embolus formation, harmful platelet aggregation, reocclusion following thrombolysis, reperfusion injury, restenosis, artherosclerlosis, stroke, myocardial infarction and unstable angina, which comprises administering to a host in need of thereof, a therapeutically effective amount of a compound of claim 17.

22. The method of claim 21, wherein the compound is administered at a dosage from about 0.001 to about 10 mg/kg of body weight per day.

23. The Form 2 polymorph of crystalline methyl-$N^3$-[2-{3-(4-formamidinophenyl)-isoxazolin-5(R)-yl}-acetyl]-$N^2$-(n-butyloxycarbonyl)-2,3-(S)-diaminopropionate which has an x-ray powder diffraction pattern having four or more 2θ values selected from the group consisting of: 6.4±0.2, 9.6±0.2, 12.4±0.2, 13.6±0.2, 18.8±0.2, 20.7±0.2, 22.6±0.2, 23.1±0.2, 25.1±0.2, 26.1±0.2, 27.3±0.2, and 28.5±0.2.

24. A pharmaceutical composition comprising a therapeutically effective amount of the compound of claim 23 and a pharmaceutically acceptable carrier.

25. The pharmaceutical composition of claim 24 which is in solid or liquid form and which contains from about 0.1 mg to about 25 mg of the compound per dose.

26. A method for inhibiting the binding of a soluble adhesive protein to platelet glycoprotein IIb/IIIa complex in a human or an animal which comprises administering to the human or animal in need thereof the compound of claim 23 in an amount sufficient to inhibit the binding of the soluble adhesive protein to the platelet glycoprotein IIb/IIIa complex.

27. A method for the treating or preventing thromoembolic disorders selected from thrombus or embolus formation, harmful platelet aggregation, reocclusion following thrombolysis, reperfusion injury, restenosis, artherosclerlosis, stroke, myocardial infarction and unstable angina, which comprises administering to a host in need thereof, a therapeutically effective amount of a compound of claim 23.

28. The method of claim 27, wherein the compound is administered at a dosage from about 0.001 to about 10 mg/kg of body weight per day.

29. A pharmaceutical composition comprising the polymorph of claim 1 and the polymorph of claim 9 and a pharmaceutically acceptable carrier.

30. A pharmaceutical composition comprising the polymorph of claim 17 and the polymorph of claim 23 and a pharmaceutically acceptable carrier.

* * * * *